US012567145B2

(12) United States Patent
Chen et al.

(10) Patent No.: US 12,567,145 B2
(45) Date of Patent: Mar. 3, 2026

(54) METHOD AND SYSTEM FOR GENERATING LABEL OF MEDICAL IMAGE

(71) Applicant: HTC Corporation, Taoyuan (TW)

(72) Inventors: I-Ting Chen, Taoyuan (TW); Yu-Shao Peng, Taoyuan (TW)

(73) Assignee: HTC Corporation, Taoyuan (TW)

( * ) Notice: Subject to any disclaimer, the term of this patent is extended or adjusted under 35 U.S.C. 154(b) by 451 days.

(21) Appl. No.: 18/298,383

(22) Filed: Apr. 11, 2023

(65) Prior Publication Data

US 2023/0326023 A1      Oct. 12, 2023

Related U.S. Application Data

(60) Provisional application No. 63/362,755, filed on Apr. 11, 2022.

(51) Int. Cl.
*G06T 7/00*          (2017.01)
*G06T 3/40*          (2024.01)
(Continued)

(52) U.S. Cl.
CPC .............. *G06T 7/0012* (2013.01); *G06T 3/40* (2013.01); *G06V 10/242* (2022.01);
(Continued)

(58) Field of Classification Search
None
See application file for complete search history.

(56) References Cited

U.S. PATENT DOCUMENTS

| 8,345,943 B2 | 1/2013 | Neemuchwala et al. |
| 11,266,480 B2 | 3/2022 | Gibby et al. |
| | (Continued) | |

FOREIGN PATENT DOCUMENTS

| CN | 104282015 B | 11/2017 |
| CN | 108461129 A | 8/2018 |
| | (Continued) | |

OTHER PUBLICATIONS

Lee June-Goo et al., "Fully Automatic Coronary Calcium Score Software Empowered by Artificial Intelligence Technology: Validation Study Using Three CT Cohorts" ,Korean journal of radiology: official journal of the Korean Radiological Society, vol. 22, No. 11, Jan. 1, 2021 (Jan. 1, 2021), p. 1764, XP093150156, ISSN: 1229-6929, DOI: 10.3348/kjr.2021.0148.
(Continued)

*Primary Examiner* — David Ometz
(74) *Attorney, Agent, or Firm* — CKC & Partners Co., LLC

(57) ABSTRACT

A medical image processing method includes the following steps. A first medical image about a first patient under a first examination condition is obtained. A second medical image about the first patient under a second examination condition is obtained. A first label corresponding to the first medical image is collected. The first label marks a lesion within the first medical image. A transformation function between the first medical image and the second medical image is calculated by aligning the first medical image with the second medical image. The transformation function is applied to convert the first label into a second label corresponding to the second medical image.

18 Claims, 8 Drawing Sheets

200 obtaining a first medical image about a first patient under a first examination condition — S210 obtaining a second medical image about the first patient under a second examination condition — S220 collecting a first label corresponding to the first medical image — S230 pre-processing the first medical image and the second medical image — S240 calculating a transformation function between the first medical image and the second medical image — S250 applying the transformation function to convert the first label into a second label corresponding to the second medical image — S260

(51) Int. Cl.

| | |
|---|---|
| *G06V 10/24* | (2022.01) |
| *G06V 10/74* | (2022.01) |
| *G16H 30/40* | (2018.01) |

(52) U.S. Cl.

CPC ........... *G06V 10/761* (2022.01); *G16H 30/40* (2018.01); *G06T 2207/10081* (2013.01); *G06T 2207/20081* (2013.01); *G06T 2207/20084* (2013.01); *G06T 2207/30016* (2013.01); *G06T 2207/30096* (2013.01)

(56) References Cited

U.S. PATENT DOCUMENTS

| | | | | |
|---|---|---|---|---|
| 2014/0029812 A1* | 1/2014 | Kriston | ..................... | G06T 7/70 382/128 |
| 2015/0294467 A1* | 10/2015 | Blumhofer | ........... | G06T 7/0012 382/131 |
| 2021/0233645 A1* | 7/2021 | Morard | ................... | G06T 7/174 |

FOREIGN PATENT DOCUMENTS

| | | |
|---|---|---|
| CN | 110377779 A | 10/2019 |
| CN | 112686865 A | 4/2021 |
| CN | 113469972 A | 10/2021 |
| CN | 114283151 A | 4/2022 |
| CN | 117174264 A * | 12/2023 |

OTHER PUBLICATIONS

The office action of the corresponding European application No. EP 23167015.9 issued on May 8, 2024.

Zhang et al., "Automatic Delineation of On-Line Head-And-Neck Computed Tomography Images: Toward On-Line Adaptive Radio-therapy", International Journal Of Radiation: Oncology Biology Physics, vol. 68, No. 2, May 9, 2007 (May 9, 2007), pp. 522-530, XP022067011, ISSN : 0360-3016, DOI: 10.1016/J.IJROBP.2007. 01.038.

Bol G H et al., "Simultaneous multi-modality ROI delineation in clinical practice" Computer Methods and Programs in Biomedicine, vol. 96, No. 2, Nov. 1, 2009 (Nov. 1, 2009), pp. 133-140, XP026521945, ISSN: 0169-2607, DOI: 10.1016/J.CMPB.2009.04.008.

The European search report of the corresponding European application No. EP 23167015.9 issued on Sep. 27, 2023.

The Office Action of the corresponding European application No. EP 23167015.9 issued on Oct. 9, 2023.

The office action of the corresponding Taiwanese application No. TW112113530 issued on Sep. 20, 2024.

* cited by examiner

IMG1

LB1

IMG2

IMG1

METHOD AND SYSTEM FOR GENERATING LABEL OF MEDICAL IMAGE

RELATED APPLICATIONS

This application claims the priority benefit of U.S. Provisional Application Ser. No. 63/362,755, filed Apr. 11, 2022, which is herein incorporated by reference.

BACKGROUND

Field of Invention

The disclosure relates to a medical image processing system and medical image processing method. More particularly, the disclosure relates to a medical image processing system and medical image processing method capable of converting image labels between medical examinations.

Description of Related Art

Several medical imaging technologies are widely used in diagnosing diseases or examining health conditions on patients. For example, X-ray imaging, computed tomography (CT) imaging and a magnetic resonance imaging (MRI) can provide critical information while diagnosing a cancer, a fracture, an internal bleeding and other symptoms.

Normally, it requires an experienced doctor or an expert to look into outcome images generated by these medical imaging technologies, and to determine whether the outcome images are normal or abnormal. Recently, some artificial intelligence (AI) systems are developed to classify examination outcomes of the medical images. In order to train an artificial intelligence agent for classifying medical images, it requires a lot of medical images and label data corresponding to these medical images. Producing correct label data on these medical images is a professional task, which is time-consuming and must be executed by personnel with medical expertise. Therefore, the label data on medical images are always recognized as scarce resources.

SUMMARY

An embodiment of the disclosure provides a medical image processing method, which includes following steps. A first medical image about a first patient under a first examination condition is obtained. A second medical image about the first patient under a second examination condition is obtained. A first label corresponding to the first medical image is collected. The first label marks a lesion within the first medical image. A transformation function between the first medical image and the second medical image is calculated by aligning the first medical image with the second medical image. The transformation function is applied to convert the first label into a second label corresponding to the second medical image.

An embodiment of the disclosure provides a medical image processing system, which includes a memory, an interface and a processor. The memory is configured to store a first medical image and a second medical image. The first medical image is captured under a first examination condition about a first patient. The second medical image is captured under a second examination condition about the first patient. The second examination condition is different from the first examination condition. The interface is configured to collect a first label corresponding to the first medical image. The first label is configured to mark a lesion within the first medical image. The processor is coupled with the interface and the memory. The processor is configured to calculate a transformation function between the first medical image and the second medical image by aligning the first medical image with the second medical image. The processor is configured to apply the transformation function for converting the first label into a second label corresponding to the second medical image.

It is to be understood that both the foregoing general description and the following detailed description are by examples, and are intended to provide further explanation of the invention as claimed.

BRIEF DESCRIPTION OF THE DRAWINGS

The disclosure can be more fully understood by reading the following detailed description of the embodiment, with reference made to the accompanying drawings as follows.

DETAILED DESCRIPTION

Figure 1:
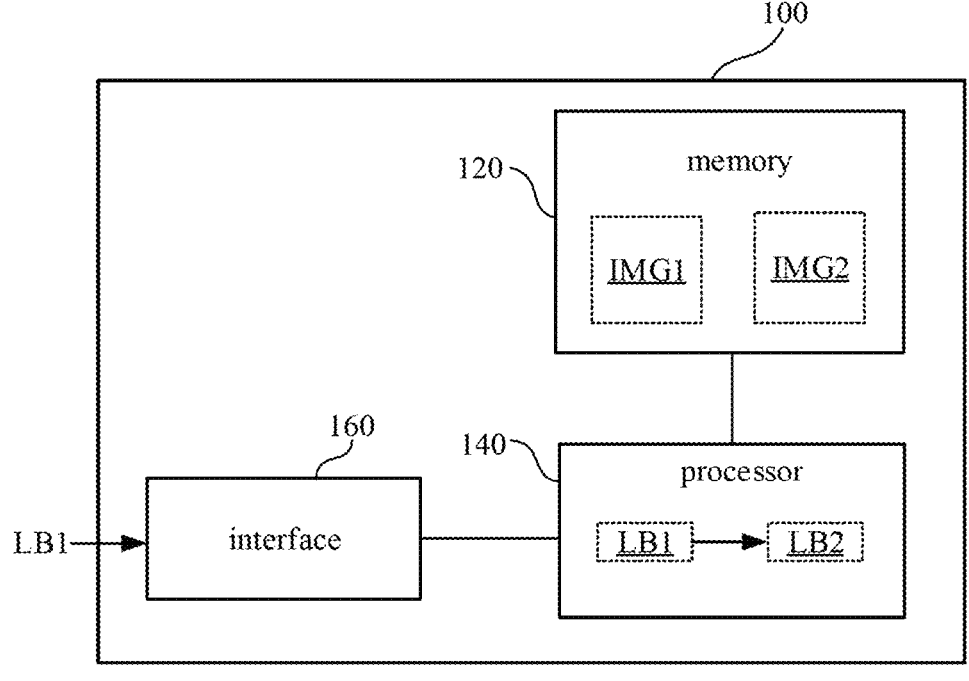
FIG. 1 is a block diagram illustrating a medical image processing system according to some embodiments of this disclosure.

Reference will now be made in detail to the present embodiments of the disclosure, examples of which are illustrated in the accompanying drawings. Wherever possible, the same reference numbers are used in the drawings and the description to refer to the same or like parts.

Reference is made to FIG. 1, which is a block diagram illustrating a medical image processing system 100 according to some embodiments of this disclosure. In some embodiments, the medical image processing system 100 is configured to convert labels between different medical images captured under different examination conditions.

As shown in FIG. 1, the medical image processing system 100 includes a memory 120, a processor 140 and an interface 160. The memory 120 is configured to store some data (e.g., medical images) and computer-executable instructions. In some embodiments, the memory 120 can include a dynamic memory, a static memory, a hard-drive and/or a flash memory. The interface 160 is configured to receive input data (e.g., an input medical image, an instruction, a voice command or a keyboard input) and/or display output content. In some embodiments, the interface 160 may include a keyboard, a displayer, a touch panel, a micro- phone, a network transceiver, a speaker, etc. The processor 140 is coupled with the memory 120 and the interface 160. In some embodiments, the processor 140 can include a central processing unit (CPU), a graphic processing unit (GPU), a tensor processing unit (TPU), an application specific integrated circuit (ASIC) or any equivalent process- ing circuit.

Figure 2B:
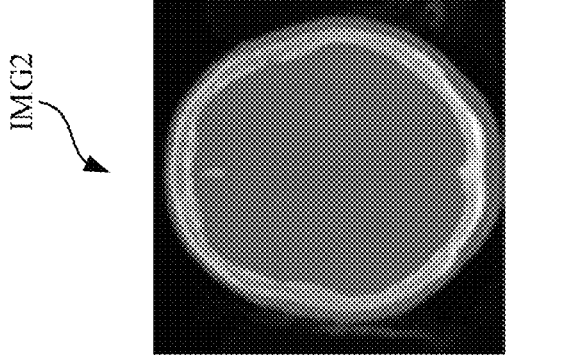
FIG. 2A and FIG. 2B are schematic diagrams illustrating an exemplary pair of the first medical image and the second medical image according to some embodiments of the disclosure.
Figure 2A:
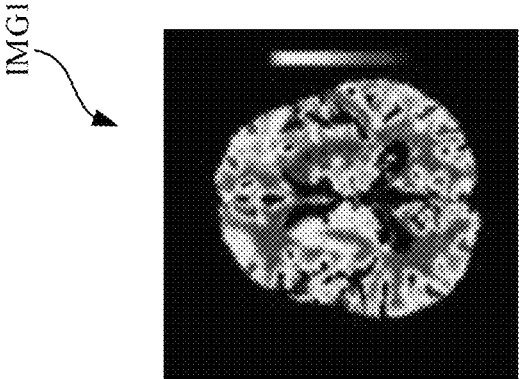

In the medical field, in order to examine a health condition of a patient, the same patient may undergo different medical imaging examinations during a visit to the hospital. These different medical imaging examinations may generate dif- ferent medical images about the same patient. As shown in FIG. 1, the memory 120 is configured to store a first medical image IMG1 and a second medical image IMG2. In some embodiments, the first medical image IMG1 is captured under a first examination condition about a first patient, and the second medical image IMG2 is captured under a second examination condition about the first patient. In other words, the first medical image IMG1 and the second medical image IMG2 are about the same patient under different examina- tion conditions. Reference is further made to FIG. 2A and FIG. 2B. FIG. 2A and FIG. 2B are schematic diagrams illustrating an exemplary pair of the first medical image IMG1 and the second medical image IMG2 according to some embodiments of the disclosure.

In some embodiments, the first medical image IMG1 under the first examination condition is captured on the first patient with dosing a contrast medium. As shown in FIG. 2A, the first medical image IMG1 is a computed tomography perfusion image about a head portion of the first patient in the example. In practical applications, the computed tomog- raphy perfusion image is a three-dimensional image. For brevity, the computed tomography perfusion image shown in FIG. 2A is one sectional view of the three-dimensional computed tomography perfusion image for demonstration.

On the other hand, the second medical image IMG2 under the second examination condition is captured on the first patient without dosing the contrast medium. As shown in FIG. 2B, the second medical image IMG2 is a non-contrast computed tomography image about the head portion of the first patient in the example. In practical applications, the non-contrast computed tomography image is a three-dimen- sional image. For brevity, the non-contrast computed tomog- raphy image shown in FIG. 2B is one sectional view of the three-dimensional non-contrast computed tomography image for demonstration.

Figure 3:
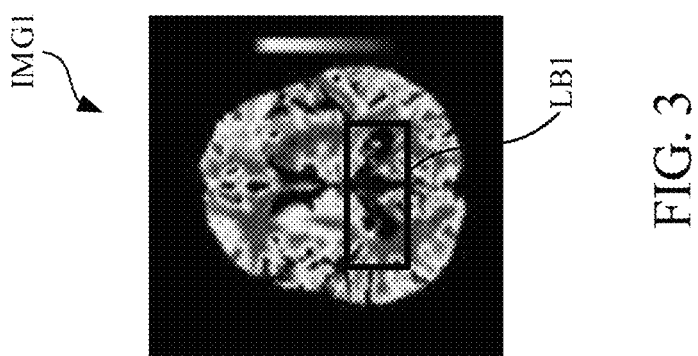
FIG. 3 is a schematic diagram illustrating a first label corresponding to the first medical image to some embodiments of the disclosure.

Based on the computed tomography perfusion image with dosing the contrast medium, it is relatively easier for medi- cal personnel (e.g., a doctor, a radiologist or a medical expert) to locate a lesion within the first medical image IMG1. For example, with dosing the contrast medium, it is easier to locate a blood leakage/blockage region within the first medical image IMG1 by the medical personnel, and the blood leakage/blockage region may lead to an ischemic stroke. Reference is further made to FIG. 3, which is a schematic diagram illustrating a first label LB1 correspond- ing to the first medical image IMG1 to some embodiments of the disclosure.

In some embodiments, the medical personnel can observe the first medical image IMG1 on the interface 160 and manually assign the first label LB1 on a specific region of the first medical image IMG1 based on their medical knowledges. The first label LB1, manually inputted by the medical personnel about the lesion in the first medical image IMG1, can be collected by the interface 160 of the medical image processing system 100 and transmitted to the processor 140. In some other embodiments, the first label LB1 can be extracted from existed medical records and imported through the interface 160 to the processor 140.

Based on the non-contrast computed tomography image without dosing the contrast medium, it is relatively harder for the medical personnel to locate a lesion within the second medical image IMG2. Because the blood leakage/blockage region is hardly visible in the second medical image IMG2, it may consume a lot of time to locate a blood leakage/ blockage region within the second medical image IMG2. Producing label data manually on the second medical image IMG2 takes a lot of time and costs a lot of money. Therefore, it is hard to find any reliable label data marking the lesion on the second medical image IMG2.

In practical applications, equipment and procedures for capturing the computed tomography perfusion image (e.g., the first medical image IMG1 as shown in FIG. 2A) are relatively complicated and expensive, in comparison with equipment and procedures for capturing the non-contrast computed tomography image (e.g., the second medical image IMG2 as shown in FIG. 2B). Some small hospitals do not have equipment for capturing computed tomography perfusion image. On the other hand, the equipment and procedures for capturing the non-contrast computed tomog- raphy image (e.g., the second medical image IMG2 as shown in FIG. 2B) are relatively accessible and common in hospitals. In some cases, it is faster and cheaper for the patient to perform a non-contrast computed tomography examination compared with a computed tomography perfu- sion examination. It is desired to be able to detect the lesion based on the non-contrast computed tomography image (i.e., the second medical image IMG2 as shown in FIG. 2B).

In some embodiments, the processor 140 of the medical image processing system 100 is able to calculate a transfor- mation function between the first medical image IMG1 and the second medical image IMG2, and utilize the transfor- mation function to convert the first label LB1 corresponding to the first medical image IMG1 into a second label LB2 corresponding to the second medical image IMG2. Further details about how to convert the first label LB1 into the second label LB2 will be discussed in following paragraphs.

Figure 4:
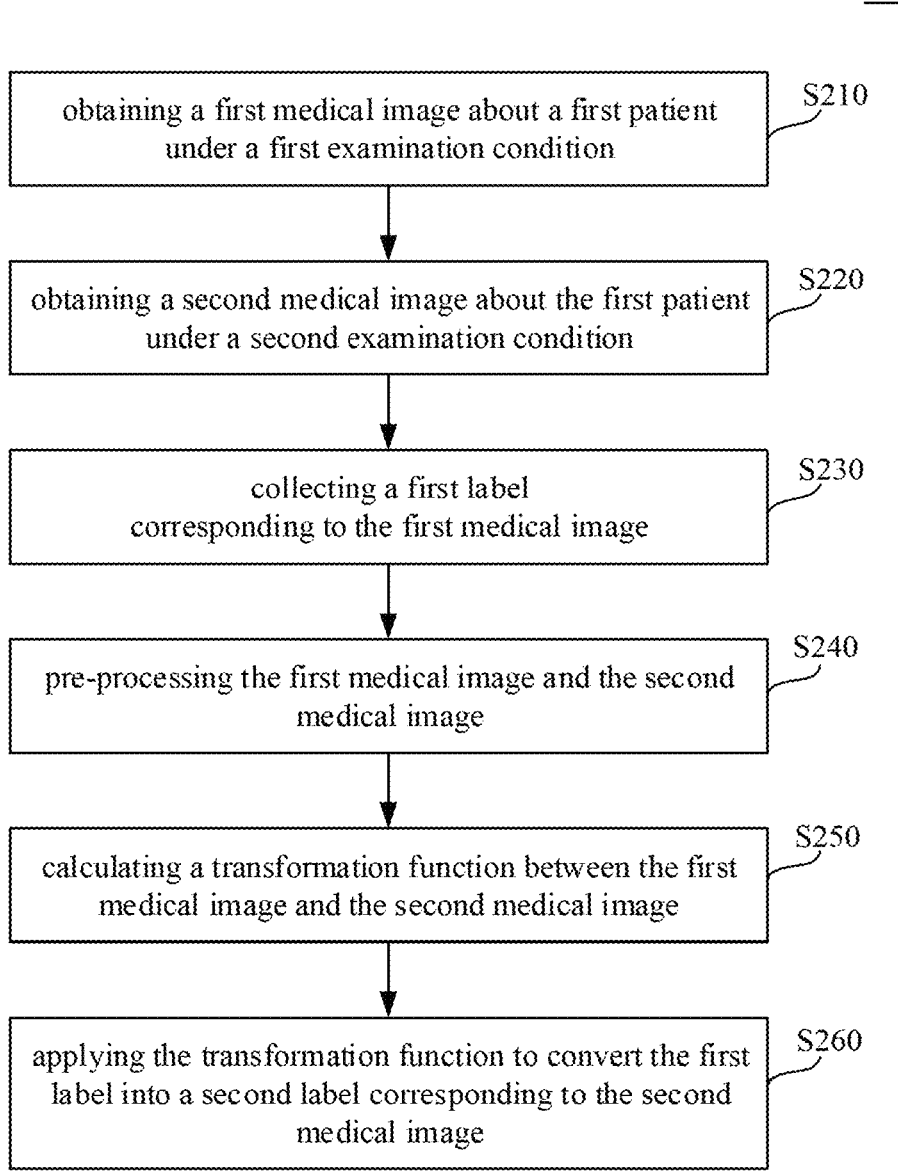
FIG. 4 is a flowchart diagram illustrating a medical image processing method according to some embodiments of the disclosure.

Reference is further made to FIG. 4, which is a flowchart diagram illustrating a medical image processing method 200 according to some embodiments of the disclosure. In some embodiments, the medical image processing method 200 in FIG. 4 can be executed by the medical image processing system 100 as shown in FIG. 1.

As shown in FIG. 1 and FIG. 4, step S210 is executed by the medical image processing system 100 for obtaining the first medical image IMG1 (referring to FIG. 2A) about the first patient under the first examination condition. In embodiments shown in FIG. 2A, the first medical image IMG1 is obtained from an external examination scanner (not shown in figures) performing a computed tomography per- fusion scanning.

As shown in FIG. 1 and FIG. 4, step S220 is executed by the medical image processing system 100 for obtaining the second medical image IMG2 (referring to FIG. 2B) about the first patient under the second examination condition. In embodiments shown in FIG. 2B, the second medical image IMG2 is obtained from an external examination scanner (not shown in figures) performing a non-contrast computed tomography scanning.

As shown in FIG. 1 and FIG. 4, step S230 is executed by the interface 160 for collecting the first label LB1 (referring to FIG. 3) corresponding to the first medical image IMG1, and the first label LB1 marks the lesion within the first medical image IMG1. The first label LB1 can be manually inputted by a doctor, a radiologist or a medical expert through the interface 160.

Figure 5:
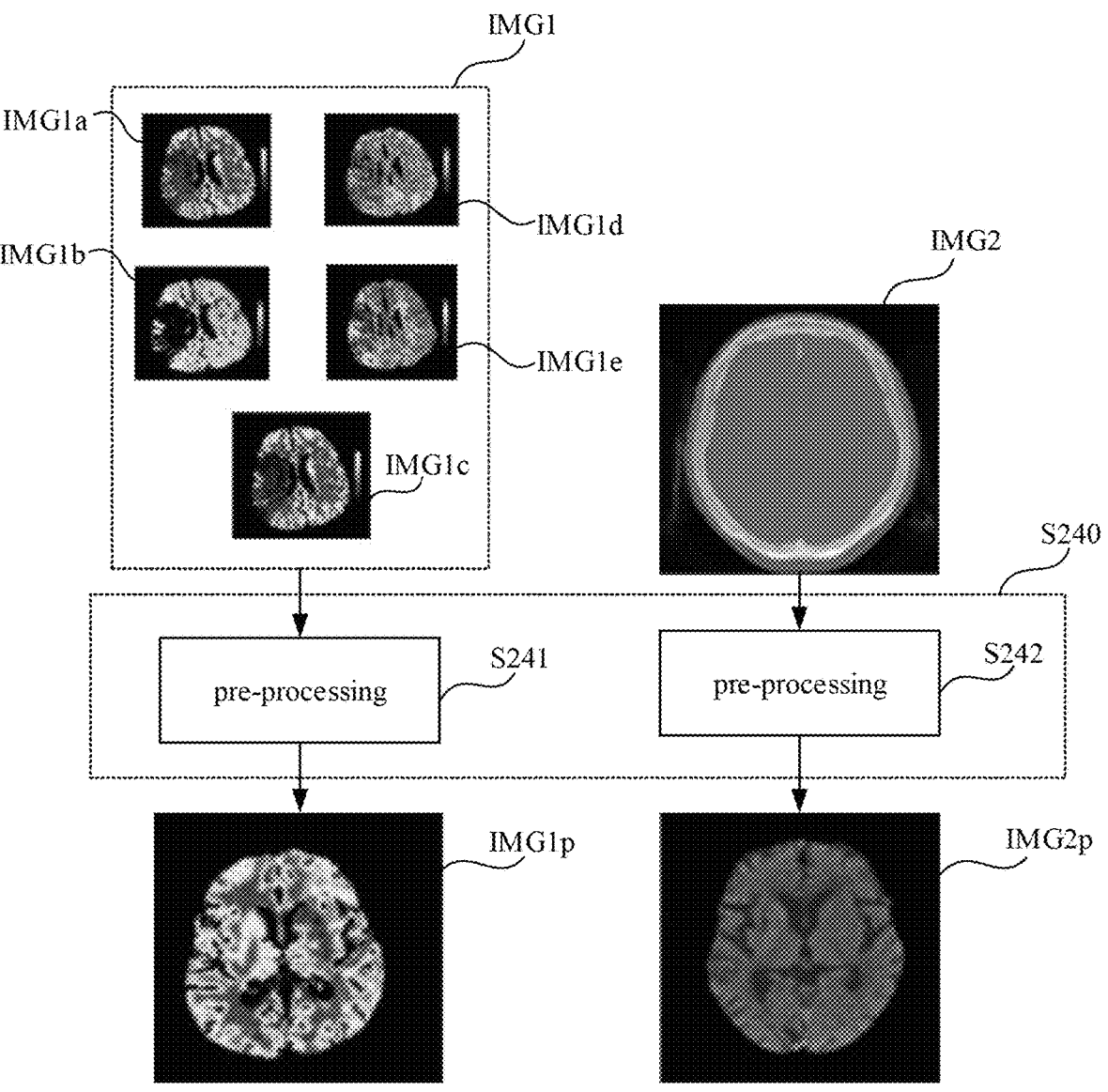
FIG. 5 is a schematic diagram illustrating pre-processing on the first medical image and the second medical image according to some embodiments in the disclosure.

In some embodiments, before calculating the transformation function between the first medical image IMG1 and the second medical image IMG2, step S240 is executed by the processor 140 for pre-processing the first medical image IMG1 and the second medical image IMG2. Reference is further made to FIG. 5. FIG. 5 is a schematic diagram illustrating pre-processing on the first medical image IMG1 and the second medical image IMG2 in step S240 according to some embodiments in the disclosure.

As shown in FIG. 5, in some embodiments, the first medical image IMG1 (i.e., the computed tomography perfusion image) may include several computed tomography perfusion subgraphs, which includes computed tomography perfusion subgraphs IMG1$a$, IMG1$b$, IMG1$c$, IMG1$d$ and IMG1$e$. These computed tomography perfusion subgraphs IMG1$a$-IMG1$e$ show brain examination results under different perfusion modalities. In some embodiments, each of the computed tomography perfusion subgraphs IMG1$a$-IMG1$e$ includes a brain perfusion result and also a color index bar located on the right side.

As shown in FIG. 5, step S240 includes two sub-steps S241 and S242. Step S241 is executed by the processor 140 for pre-processing the first medical image IMG1 for cancelling a first noise feature in the first medical image IMG1 while maintaining a first target feature in the first medical image IMG1. In some embodiments, during step S241, the color index bars in the computed tomography perfusion subgraphs IMG1$a$-IMG1$e$ are regarded as noise features and cancelled by the processor 140. In some embodiments, the processor 140 can utilize a rectangle mask (e.g., with a width of one pixel and a height equal to IMG1$a$-IMG1$e$) to scan over different parts on these computed tomography perfusion subgraphs IMG1$a$-IMG1$e$. The processor 140 detects the pixel values located in the rectangle mask in different scanning rounds. When pixel values located in the rectangle mask in three adjacent scanning rounds are no image data (or all dark pixels), with colored data and no image data (or all dark pixels) in sequence, the processor 140 is able to detect the color index bar. The processor 140 can cancel the color index bar in the computed tomography perfusion subgraphs IMG1$a$-IMG1$e$ by filling the color index bars with the background color. On the other hand, the brain perfusion results within the computed tomography perfusion subgraphs IMG1$a$-IMG1$e$ are regarded as target features and maintained by the processor 140.

Besides cancelling the color index bars, during step S241, the processor 140 further performs a union operation to combine the computed tomography perfusion subgraphs IMG1$a$-IMG1$e$ into a processed first medical image IMG1$p$. The union operation is performed by applying a logical "OR" to combine the computed tomography perfusion subgraphs IMG1$a$-IMG1$e$. In this case, pixel data of the brain perfusion results in five computed tomography perfusion subgraphs IMG1$a$-IMG1$e$ are integrated into the processed first medical image IMG1$p$ as shown in FIG. 5.

On the other hand, the non-contrast computed tomography image may include image data about skull, scalp and brain tissues. As shown in FIG. 5, step S242 is executed by the processor 140 for pre-processing the second medical image IMG2 for cancelling a second noise feature in the second medical image IMG2 while maintaining a second target feature in the second medical image IMG2. In this case, the image data about skull and the image data about scalp are regard as the noise features, and cancelled by the processor in step S242. In this case, the image data about brain tissues are regard as the target features and maintained by the processor 140 in step S242, so as to generate a processed second medical image IMG2$p$ as shown in FIG. 5.

Figure 6:
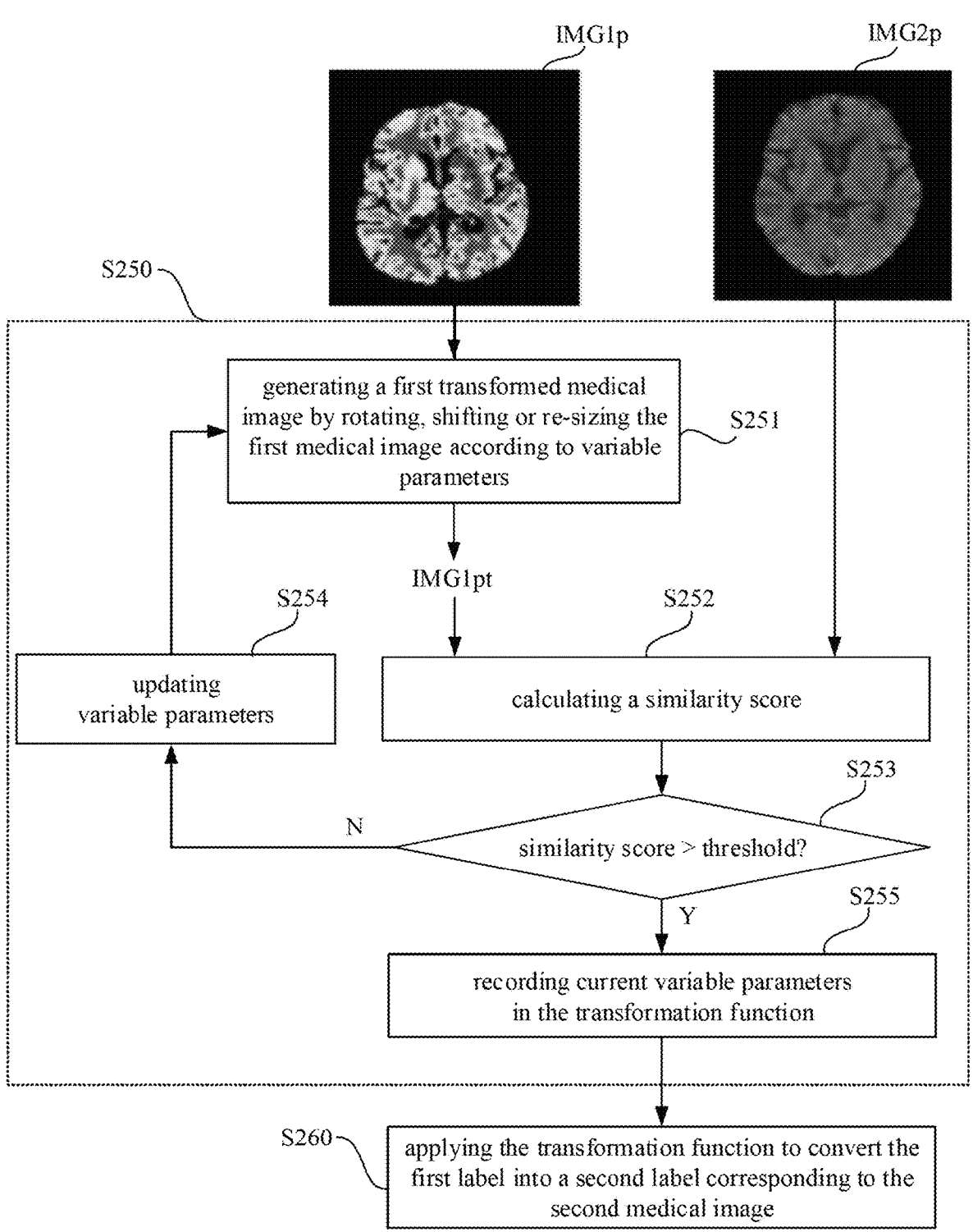
FIG. 6 is a schematic diagram illustrating operations for calculating the transformation function according to some embodiments in the disclosure.

As shown in FIG. 4, step S250 is executed by the processor 140, to calculating a transformation function between the first medical image IMG1 and the second medical image IMG2. Reference is further made to FIG. 6, which is a schematic diagram illustrating operations in step S250 for calculating the transformation function according to some embodiments in the disclosure. Step S250 includes sub-steps S251 to S255. As shown in FIG. 6, in step S250, the processor 140 calculate the transformation function by aligning the processed first medical image IMG1$p$ and the processed second medical image IMG2$p$.

Step S251 is executed by the processor 140 for generating a first transformed medical image IMG1$pt$ by rotating, shifting and/or re-sizing the processed first medical image IMG1$p$ according to variable parameters. For example, the variable parameters include rotating angles ($\theta$x1, $\theta$y1, $\theta$z1), shifting displacements (Dx1, Dy1, Dz1) and/or a re-sizing ratio (R1). The processor 140 is configured to rotate the processed first medical image IMG1$p$ according to the rotating angles ($\theta$x1, $\theta$y1, $\theta$z1), shift the processed first medical image IMG1$p$ according to the shifting displacements (Dx1, Dy1, Dz1) and/or re-size the processed first medical image IMG1$p$ according to the re-sizing ratio (R1), so as to generate the first transformed medical image IMG1$pt$.

Afterward, step S252 is executed by the processor 140 to calculate a similarity score by comparing the first transformed medical image IMG1$pt$ and the processed second medical image IMG2$p$. In this case, when the target features in the first transformed medical image IMG1$pt$ are highly overlapped with the target features in the processed second medical image IMG2$p$, the similarity score will be higher. On the other hand, when the target features in the first transformed medical image IMG1$pt$ are mismatched from the target features in the processed second medical image IMG2$p$, the similarity score will be lower. In some embodiments, the similarity score between the first transformed medical image IMG1$pt$ and the processed second medical image IMG2$p$ can be calculated by a Mattes Mutual Information algorithm.

Step S253 is executed by the processor 140 to check whether the similarity score satisfies a similarity threshold or not. The similarity threshold can be predetermined (e.g., 50%, 70% or 90%) or dynamically assigned (e.g., a relatively high similarity score in three minutes).

If the current similarity score is below the similarity threshold, step S254 is executed by the processor 140 to update the variable parameters. For example, the processor 140 updates the rotating angles into ($\theta$x2, $\theta$y2, $\theta$z2), updates the shifting displacements into (Dx2, Dy2, Dz2) and/or updates the re-sizing ratio into (R2). In some embodiments, updating the variable parameters in step S254 can be performed based on a Gradient Descend algorithm. Step S251 and step S252 is executed again based on the updated variable parameters. In step S251, the processor 140 re-generates the first transformed medical image IMG1$pt$ according to the update variable parameters, including the rotating angles ($\theta$x2, $\theta$y2, $\theta$z2), the shifting displacements (Dx2, Dy2, Dz2) and/or updates the re-sizing ratio into (R2). In step S252, the processor 140 re-calculates the similarity score between the first transformed medical image IMG1*pt* and the processed second medical image IMG2*p*.

Steps S251 to S254 will be repeated until the similarity score exceeds the similarity threshold. By repeating the steps S251 to S254, the target features in the first transformed medical image IMG1*pt* are rotated, shifted, re-sized to be overlapped with the target features in the processed second medical image IMG2*p*. If the similarity score is high, it means that the locations and sizes of target features shown in the first transformed medical image IMG1*pt* are highly overlapped with the target features shown in the processed second medical image IMG2*p*. If the similarity score exceeds the similarity threshold, step S255 is executed by the processor 140 to recording the current variable parameters as the transformation function.

It is noticed that, the first medical image IMG1 and the second medical image IMG2 are images about the same patient captured under different examination conditions. Therefore, it may include a rotation difference, a displacement, a sizing difference while capturing the first medical image IMG1 and the second medical image IMG2. If the first label LB1 on the first medical image IMG1 is directly duplicated to the same position onto the second medical image IMG2, the duplicated label may be placed at a wrong position away from the lesion in the second medical image IMG2. In this case, the transformation function is able to calibrate a rotation difference, a displacement, a sizing difference between the first medical image IMG1 and the second medical image IMG2.

In other embodiments of step S250, it is also feasible to generate the transformation function by inverting an inverse transform function. The inverse transform function can be generated through processes similar to steps S251 through 255, but with the roles of the processed first medical image IMG1*p* and the processed second medical image IMG2*p* being swapped in the flowchart of FIG. 6. For example, the processor 140 can generate a second transformed medical image by rotating, shifting and/or re-sizing the processed second medical image IMG2*p* according to variable parameters. Then, the similarity score is calculated by comparing the target features in second transformed medical image and the target features in the processed first medical image IMG1*p*. The processor 140 updates the variable parameters and regenerates the second transformed medical image according to the update variable parameters, until the similarity score exceeds the similarity threshold. As the similarity score exceeds the similarity threshold, the processor 140 records the current variable parameters as the inverse transformation function. In this situation, the processor executes an additional step to invert the inverse transformation function in order to generate the transformation function.

Figure 7:
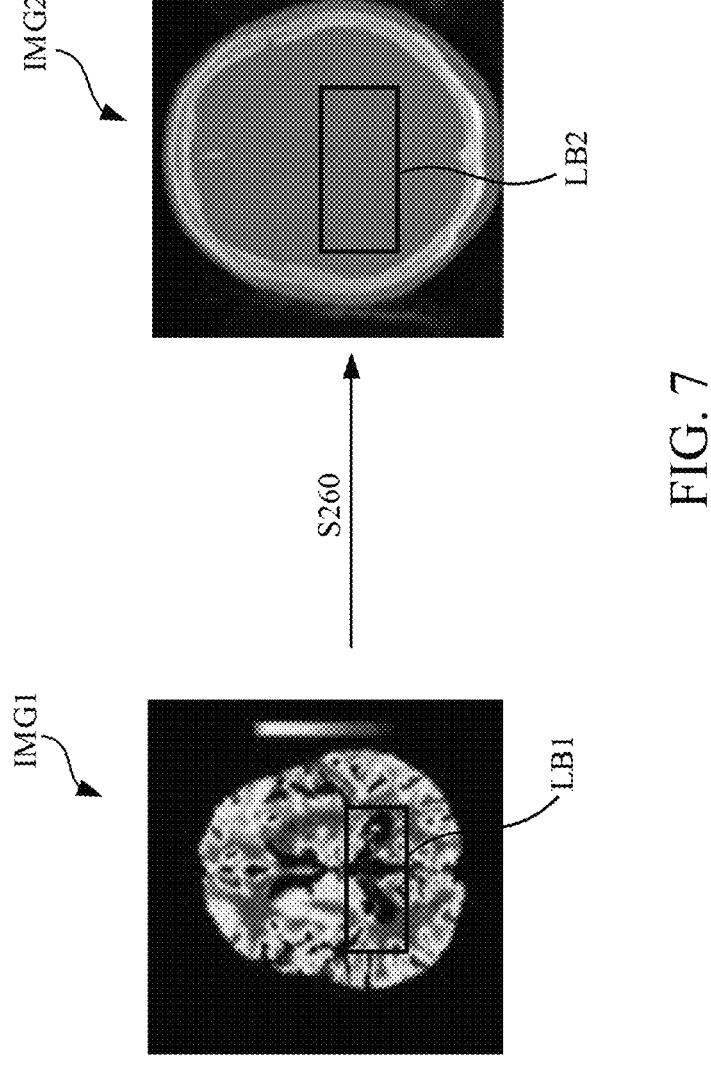
FIG. 7 is a schematic diagram illustrating the transformation of labels between the first medical image and the second medical image according to some embodiments in the disclosure.

Reference is further made to FIG. 7. FIG. 7 is a schematic diagram illustrating the transformation of labels between the first medical image IMG1 and the second medical image IMG2 according to some embodiments in the disclosure. As shown in FIG. 1, FIG. 4 and FIG. 7, step S260 is executed by the processor 140 for applying the transformation function to convert the first label LB1 into a second label LB2 corresponding to the second medical image IMG2. As shown in FIG. 7, an orientation, a location and a size of the second label LB2 on the second medical image IMG2 is adjusted by the transformation function and are different from the first label LB1 on the first medical image IMG1. In this case shown in FIG. 7, the second label LB2 is slightly larger than the first label LB1, and the second label LB2 is moved toward a top side of the second medical image IMG2 compared to the first label LB1.

The relationships between the first label LB1 and the second label LB2 are not limited to the example shown in FIG. 7. The relationships between the first label LB1 and the second label LB2 are decided by the transformation function calculated in step S250.

It is noticed that, in aforesaid embodiments, the first medical image IMG1 is demonstrated as the computed tomography perfusion image with dosing the contrast medium and the second medical image IMG2 is demonstrated as the non-contrast computed tomography image without dosing the contrast medium. This disclosure is not limited thereto. In some other embodiments, the first medical image IMG1 under the first examination condition and the second medical image IMG2 under the second examination condition are captured by different examination scanners. In an example, the first medical image IMG1 can be a computed tomography (CT) image captured by a computed tomography scanner, and the second medical image IMG2 can be an X-ray image captured by an X-ray scanner. In another example, the first medical image IMG1 can be a magnetic resonance imaging (MRI) image captured by a magnetic resonance imaging scanner, and the second medical image IMG2 can be the computed tomography image captured by the computed tomography scanner. Similarly to embodiments shown in FIG. 4 to FIG. 7, the processor 140 of the medical image processing system 100 is able to convert the first label LB1 (manually assigned by the medical personnel) on the first medical image IMG1 into the second label LB2 on the second medical image IMG2.

Based on the medical image processing system 100 and the medical image processing method 200 shown in aforesaid embodiments in FIG. 1 to FIG. 7, the medical image processing system 100 and the medical image processing method 200 are able convert labels between different medical images captured under different examination conditions, and produce a reliable label on the second medical image IMG2 under the second examination condition. Even though it is hard to collect/produce a manual label of the second medical image IMG2 by the medical personnel, the medical image processing system 100 and the medical image processing method 200 can convert the second label LB2 from the first label LB1, which is relatively easier to label by the medical personnel. In this case, the medical image processing system 100 and the medical image processing method 200 are able to solve a scarcity issue of the second medical label LB2 on the second medical image IMG2. In some embodiments, the medical image processing system 100 is able to repeat the medical image processing method 200 shown in FIG. 4 to produce multiple second labels LB2 corresponding to different second medical images IMG2 (e.g., the non-contrast computed tomography image) captured under the second examination condition. In some embodiments, the second labels LB2 and the second medical images IMG2 can be utilized to train a neural network model for predicting a lesion based on non-contrast computed tomography images.

Figure 8:
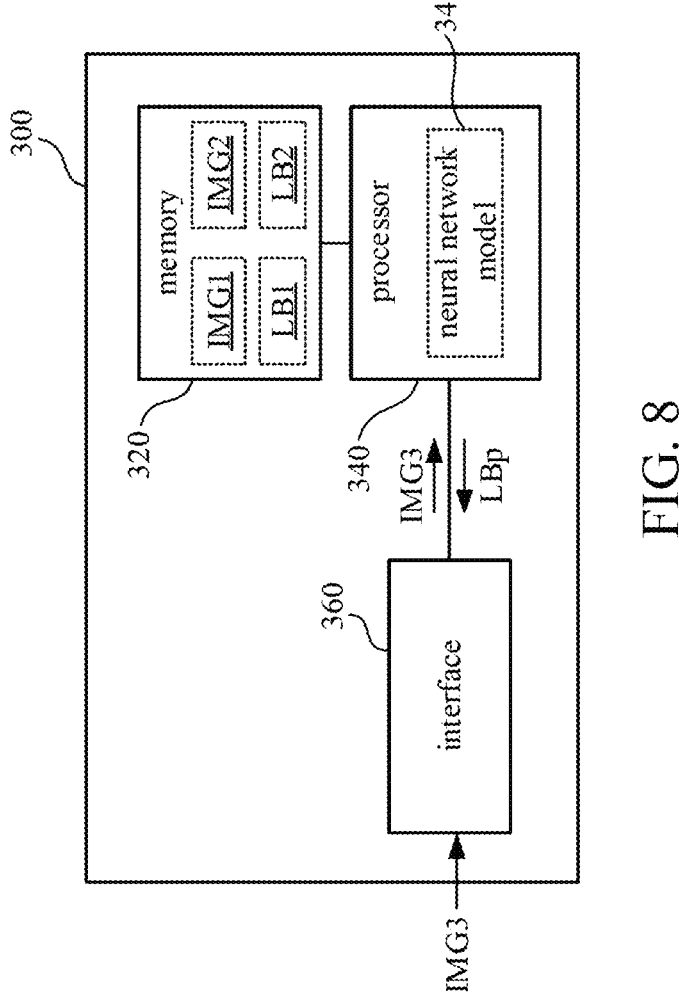
FIG. 8 is a block diagram illustrating a medical image processing system according to some embodiments of this disclosure.
Figure 9:
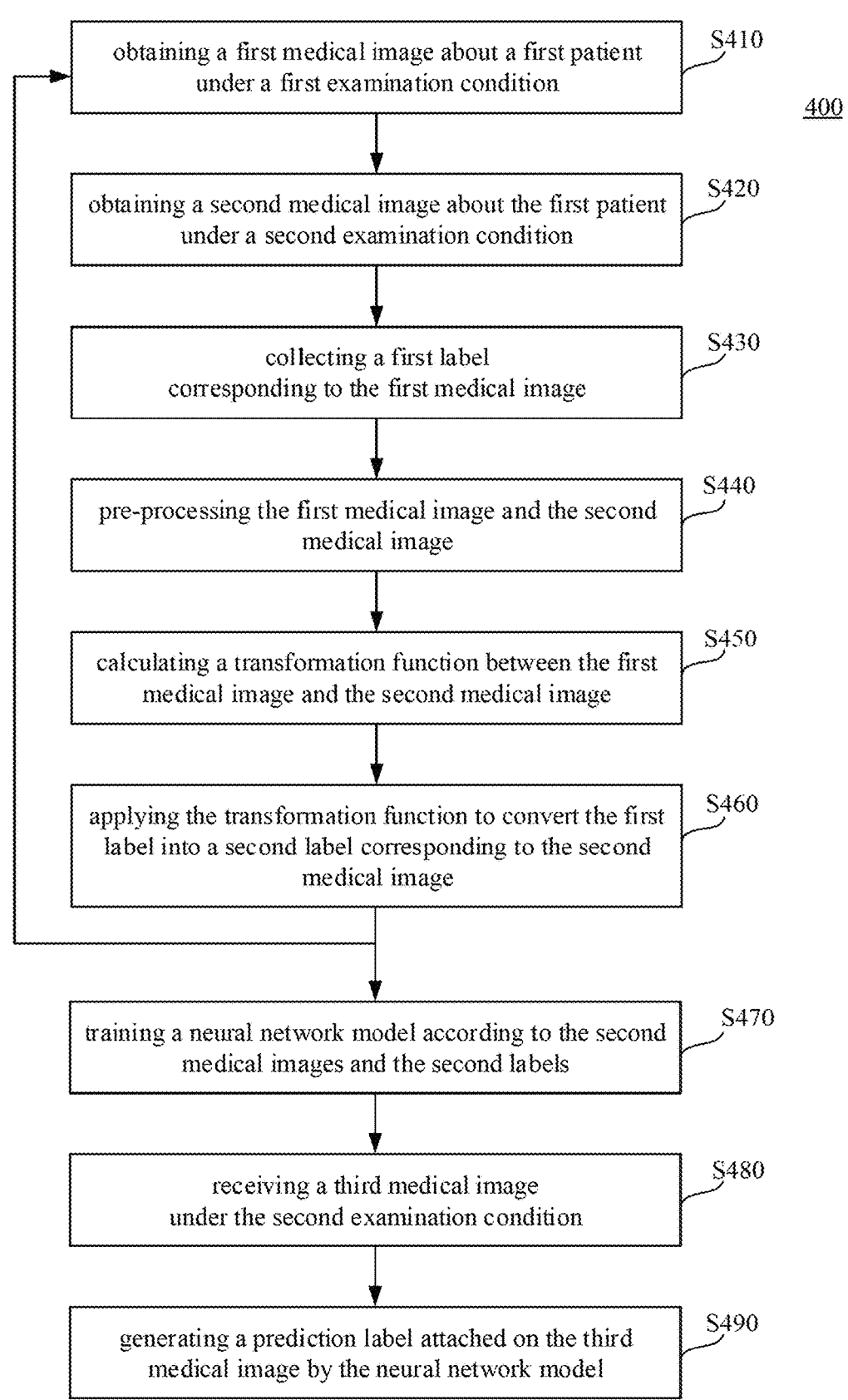
FIG. 9 is a flowchart diagram illustrating a medical image processing method according to some embodiments of the disclosure.

Reference is further made to FIG. 8 and FIG. 9. FIG. 8 is a block diagram illustrating a medical image processing system 300 according to some embodiments of this disclosure. FIG. 9 is a flowchart diagram illustrating a medical image processing method 400 according to some embodiments of the disclosure. As shown in FIG. 8, the medical image processing system 300 includes a memory 320, a processor 340 and an interface 360.

Similar to aforesaid embodiments in FIG. 1 to FIG. 7, the processor 340 of the medical image processing system 300 in FIG. 8 is able to executed steps S410 to S460 shown in FIG. 9 for calculating a transformation function between the first medical image IMG1 and the second medical image IMG2, and utilizing the transformation function to convert the first label LB1 corresponding to the first medical image IMG1 into a second label LB2 corresponding to the second medical image IMG2. The details about the calculating the transformation function and converting the first label LB1 into the second label LB2 in steps S410 to S460 can be referred the aforesaid embodiments in steps S210 to S260, and are not repeated here.

In some embodiments, the processor 340 is configured to repeat the steps S410 to S460 in FIG. 9 multiple times to produce multiple second labels LB2 corresponding to different second medical images IMG2 (e.g., the non-contrast computed tomography image) captured under the second examination condition. The second medical images IMG2 and corresponding second labels LB2 are utilized as training data. As shown in FIG. 8 and FIG. 9, step S470 is executed by the processor 340 for training the neural network model 342 according to the second medical images IMG2 and the second labels LB2.

The neural network model 342 can be implemented by a convolutional neural network for lesion classification or lesion detection. The second medical images IMG2 and corresponding second labels are utilized as ground truth to train the convolutional neural network. When a prediction label generated by the neural network model 342 matches with the second label LB2, a reward signal can be provided to the neural network model 342. When a prediction label generated by the neural network model 342 fails to match with the second label LB2, a punish signal can provided to the neural network model 342.

When the training is complete, the neural network model 342 is capable of predicting a lesion label from a medical image captured under the second examination condition. For example, the neural network model 342 is capable of predicting a lesion label based on a non-contrast computed tomography image.

As shown in FIG. 8 and FIG. 9, in step S480, the interface 360 is configured to receive a third medical image IMG3 captured the second examination condition. For example, the third medical image IMG3 can be a non-contrast computed tomography image about a second patient. The second patient can be different from the first patient corresponding to the first medical image IMG1 and the second medical IMG2.

As shown in FIG. 8 and FIG. 9, step S490 is executed by the processor 340, and the processor 340 utilizes the neural network model 342 to generate a prediction label LBp attached on the third medical image IMG3. The prediction label LBp and the third medical image IMG3 can be displayed on the interface 360, such that the second patient or the medical personnel can acknowledge the prediction label LBp generated by the neural network model 342.

In practical applications, the equipment and procedures for capturing the non-contrast computed tomography image (e.g., the second medical image IMG2 as shown in FIG. 2B) are relatively accessible and common in hospitals. In some cases, it is faster and cheaper for the patient to perform a non-contrast computed tomography examination compared with a computed tomography perfusion examination. The neural network model 342 of the medical image processing system 300 is able to generate the prediction label LBp based on the non-contrast computed tomography image. It is beneficial for the patient and the hospital to diagnosis the second patient based on a faster and cheaper medical examination.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A medical image processing method, comprising:
obtaining a first medical image about a first patient under a first examination condition;
obtaining a second medical image about the first patient under a second examination condition different from the first examination condition,
wherein the first medical image under the first examination condition is captured on the first patient with dosing a contrast medium, and the second medical image under the second examination condition is captured on the first patient without dosing the contrast medium;
collecting a first label corresponding to the first medical image, the first label marking a lesion within the first medical image;
calculating a transformation function between the first medical image and the second medical image by aligning the first medical image with the second medical image; and
applying the transformation function to convert the first label into a second label corresponding to the second medical image.

2. The medical image processing method as claimed in claim 1, wherein calculating the transformation function comprises:
generating a first transformed medical image by rotating, shifting or re-sizing the first medical image according to first variable parameters;
calculating a similarity score between the first transformed medical image and the second medical image; and
in response to the similarity score exceeding a similarity threshold, recording the first variable parameters in the transformation function.

3. The medical image processing method as claimed in claim 2, wherein calculating the transformation function further comprises:
in response to the similarity score below the similarity threshold, updating the first variable parameters into second variable parameters;
re-generating the first transformed medical image according to the second variable parameters; and
re-calculating the similarity score between the first transformed medical image and the second medical image.

4. The medical image processing method as claimed in claim 1, wherein, before calculating the transformation function, the medical image processing method further comprises:

pre-processing the first medical image for cancelling a first noise feature in the first medical image while maintaining a first target feature in the first medical image; and pre-processing the second medical image for cancelling a second noise feature in the second medical image while maintaining a second target feature in the second medical image.

5. The medical image processing method as claimed in claim 1, wherein the first medical image comprises at least one computed tomography perfusion image about a head portion of the first patient, the second medical image comprises a non-contrast computed tomography image about the head portion of the first patient.

6. The medical image processing method as claimed in claim 1, wherein the first medical image under the first examination condition and the second medical image under the second examination condition are captured on the first patient by different examination scanners.

7. The medical image processing method as claimed in claim 1, wherein the first label corresponding to the first medical image is manually inputted by a doctor, a radiologist or a medical expert.

8. The medical image processing method as claimed in claim 1, further comprising:

training a neural network model according to the second medical image and the second label.

9. The medical image processing method as claimed in claim 8, further comprising:

receiving a third medical image under the second examination condition; and generating a prediction label attached on the third medical image by the neural network model.

10. A medical image processing system, comprising:

a memory, configured to store a first medical image and a second medical image, wherein the first medical image is captured under a first examination condition about a first patient, the second medical image is captured under a second examination condition about the first patient, the second examination condition is different from the first examination condition, wherein the first medical image under the first examination condition is captured on the first patient with dosing a contrast medium, and the second medical image under the second examination condition is captured on the first patient without dosing the contrast medium;

an interface, configured to collect a first label corresponding to the first medical image, wherein the first label is configured to mark a lesion within the first medical image; and a processor, coupled with the interface and the memory, wherein the processor is configured to calculate a transformation function between the first medical image and the second medical image by aligning the first medical image with the second medical image, the processor is configured to apply the transformation function for converting the first label into a second label corresponding to the second medical image.

11. The medical image processing system as claimed in claim 10, wherein the processor is configured to generate a first transformed medical image by rotating, shifting or re-sizing the first medical image according to first variable parameters, the processor is configured to calculate a similarity score between the first transformed medical image and the second medical image, in response to the similarity score exceeding a similarity threshold, the processor is configured to record the first variable parameters as the transformation function.

12. The medical image processing system as claimed in claim 11, wherein, in response to the similarity score below the similarity threshold, the processor is configured to update the first variable parameters into second variable parameters, the processor is configured to re-generate the first transformed medical image according to the second variable parameters, the processor is configured to re-calculate the similarity score between the first transformed medical image and the second medical image.

13. The medical image processing system as claimed in claim 10, wherein, the processor is configured to pre-process the first medical image for cancelling a first noise feature in the first medical image while maintaining a first target feature in the first medical image before calculating the transformation function, the processor is configured to pre-process the second medical image for cancelling a second noise feature in the second medical image while maintaining a second target feature in the second medical image before calculating the transformation function.

14. The medical image processing system as claimed in claim 10, wherein the first medical image comprises at least one computed tomography perfusion image about a head portion of the first patient, the second medical image comprises a non-contrast computed tomography image about the head portion of the first patient.

15. The medical image processing system as claimed in claim 10, wherein the first medical image under the first examination condition and the second medical image under the second examination condition are captured by different examination scanners.

16. The medical image processing system as claimed in claim 10, wherein the first label corresponding to the first medical image is manually inputted by a doctor, a radiologist or a medical expert.

17. The medical image processing system as claimed in claim 10, wherein the processor is configured to train a neural network model according to the second medical image and the second label.

18. The medical image processing system as claimed in claim 17, wherein the interface is configured to receive a third medical image under the second examination condition, the processor is configured to execute the neural network model for generating a prediction label attached on the third medical image.

* * * * *